US008553233B2

(12) United States Patent
Newman

(10) Patent No.: US 8,553,233 B2
(45) Date of Patent: Oct. 8, 2013

(54) METHOD AND APPARATUS FOR THE REMOTE NONDESTRUCTIVE EVALUATION OF AN OBJECT USING SHEAROGRAPHY IMAGE SCALE CALIBRATION

(71) Applicant: John W. Newman, Newtown Square, PA (US)

(72) Inventor: John W. Newman, Newtown Square, PA (US)

( * ) Notice: Subject to any disclaimer, the term of this patent is extended or adjusted under 35 U.S.C. 154(b) by 0 days.

(21) Appl. No.: 13/731,085

(22) Filed: Dec. 30, 2012

(65) Prior Publication Data
US 2013/0114088 A1    May 9, 2013

Related U.S. Application Data

(63) Continuation of application No. PCT/US2011/042673, filed on Jun. 30, 2011.

(51) Int. Cl.
*G01B 9/02* (2006.01)

(52) U.S. Cl.
USPC .......................................... 356/520

(58) Field of Classification Search
USPC ................................. 356/450–521
See application file for complete search history.

(56) References Cited

U.S. PATENT DOCUMENTS

| | | | | |
|---|---|---|---|---|
| 5,481,356 A | * | 1/1996 | Pouet et al. | 356/35.5 |
| 5,543,916 A | * | 8/1996 | Kachanov | 356/451 |
| 5,923,425 A | * | 7/1999 | Dewa et al. | 356/520 |
| 6,153,889 A | | 11/2000 | Jones | |
| 6,246,483 B1 | | 6/2001 | Smith | |
| 6,674,531 B2 | * | 1/2004 | Mahner | 356/457 |
| 7,083,327 B1 | | 8/2006 | Shepard | |
| 7,283,251 B1 | * | 10/2007 | Tansey | 356/512 |
| 2001/0050772 A1 | | 12/2001 | Meinlschmidt et al. | |
| 2005/0157313 A1 | * | 7/2005 | Mendlovic et al. | 356/520 |

OTHER PUBLICATIONS

Hung, Y.Y., "Shearography for Non-destructive Evaluation of Composite Structures" Optics and Lasers in Engineering, vol. 24, pp. 161-182, 1996.
International Search Report dated Feb. 29, 2012 for corresponding PCT/US2011/042673 filed Jun. 30, 2011.

\* cited by examiner

*Primary Examiner* — Tarifur Chowdhury
*Assistant Examiner* — Michael P Lapage
(74) *Attorney, Agent, or Firm* — The Patentwise Group, LLC

(57) ABSTRACT

A method and apparatus for the remote nondestructive evaluation of an object such as a wind turbine blade involves applying mechanical and/or thermal stress to the object and then scanning the object using long-range thermographic and/or laser interferometric imaging. The laser interferometric imaging is preferably performed by a long range shearography camera capable of imaging deformation derivatives at long distances coupled with a blade stressing mechanism incorporating either thermal or internal blade pressurization for the purpose of detecting remotely and at high speed, changes in the structural integrity of an installed wind turbine blade.

24 Claims, 11 Drawing Sheets

METHOD AND APPARATUS FOR THE REMOTE NONDESTRUCTIVE EVALUATION OF AN OBJECT USING SHEAROGRAPHY IMAGE SCALE CALIBRATION

This is a continuation of International Patent Application PCT/US2011/042673, filed Jun. 30, 2011, the entire disclosure of which is hereby incorporated by reference as if set forth fully herein.

BACKGROUND OF THE INVENTION

1. Field of the Invention

This invention relates to the field of nondestructive evaluation and testing, and in particular to the nondestructive testing of composite blades for wind turbine electricity generators.

2. Description of the Related Technology

Electric power generation from wind has been growing at a rate of 20 to 30% per year, and it is one of the fastest growing market segments in the power industry. According to American Wind Energy Association statistics for 2009, over 10,000 megawatts (MW) of wind power was installed in the United States. The current U.S. wind power capacity is over 35,000 MW with wind providing 39% of all new generating capacity in 2009. The development of U.S. wind energy resources is envisioned as one of the key enablers in meeting future renewable energy generation goals. Presently, the primary focus has been on development, installation, and start-up of wind energy resources. The future success of wind power will depend on consistent, reliable operation, and cost-effective maintenance of the wind assets.

The current generation of megawatt sized wind turbines are up scaled versions of earlier large kilowatt sized designs. Wind turbine towers are taller and the rotor diameters larger in order to capture as much wind energy possible; and the upsizing trend will continue. Increasing wind turbine size and output has resulted in issues with wind turbine reliability. Wind turbine components are failing prematurely which results in increased maintenance costs and downtime; and loss of revenue. Periodic maintenance inspections are performed on major wind turbine components; however, these inspections do not always identify the conditions leading to failure. Three wind turbine components with the highest incidence of failure are the gearboxes, generators, and blades. These components also have the highest cost consequences from a failure due to high costs for replacement parts, high cost to implement remedial actions (crane costs), and lost revenue caused by extended and unplanned down time.

Currently, there are no regulations, codes, or standards to regulate the operation and maintenance of wind turbines or their components. Wind asset owner/operators periodically inspect major components in accordance with the wind turbine manufacturer's or internal recommendations. Due to their size and access, periodic inspection of wind turbine blades is more difficult. Typically, the blades are visually inspected by maintenance personnel who are suspended by ropes, or use special platforms to traverse up or down the blade. These personnel perform visual examinations of the exterior surfaces for detection of flaws and damage that could be detrimental to the operability of the blade. In some cases, personnel may crawl through the interior of blade by accessing the rotor hub area to visually examine the internal structural of the blade. Recently, some jurisdictions have considered these up tower internal blade examinations to be "confined space" entries and imposed restrictions on internal blade examinations.

While the performance of periodic visual examinations of wind turbine blades is a good practice, most visual examinations are limited to the extent of flaws or damage detected since it cannot detect flaws or determine the condition of the structure underneath the blade surfaces. In addition, the quality of the examination can be highly dependent on the experience of the examination personnel; access, distance, and angle to the examination surface, and available lighting. In general, visual examination is a viable technique for determining the general condition of the blade, but may not be adequate to assess the overall structural integrity of the blade.

Wind turbine blades are aerodynamically designed structures that are constructed primarily of fiberglass or carbon fiber reinforced composite materials. The manufacture of these large composite structures is a difficult process that is normally performed with skilled manual labor. Wind turbine blades are typically constructed in two halves. Each blade half consists of an exterior skin constructed of multiple layers of fiberglass or carbon fiber material bonded to structural elements. These structural elements, such as spars and webs, add strength and rigidity to the blade to transfer the wind load back through the rotor hub, to spin the turbine/generator. The two blade halves with structural elements are assembled and bonded together using an epoxy type resin to form a bond between the mating surfaces of the two halves.

During the blade manufacturing process, fabrication flaws may occur due to manufacturing process and tolerance anomalies or problems during the resin addition and bonding process. The fabrication flaws include:

Delamination between layers of composite material,
Wrinkles, or waviness between layers of composites material,
Lack of bond or de-bonds between bond lines of structural elements and leading and trailing edges of blade.

Due to the complexities in the blade manufacturing process, most blades contain some type of fabrication flaw before they enter into service. Many fabrication flaws are not visible to the surface, and visual examination is not effective method to detect and assess the effect of the fabrication flaws on the blade during in-service conditions.

Visual examinations will provide information on the general condition of the visually accessible surfaces of a recently manufactured or an in-service wind turbine blade. However, the performance of visual examinations may be variable and subjective; and the information may not be sufficient to adequately assess the overall integrity of the blade. A small flaw visually observed on the blade surface may not be indicative of extensive damage in the structure underneath the blade skin. Thus, in order to perform a more comprehensive assessment of a blade's structural integrity, the examination should be capable of detecting flaws at or below the surface, or through the volume of blade.

Other NDE methods are available and used for wind turbine blade inspections that may provide enhanced information about the structural integrity of a blade. These methods consist of two general categories: 1) surface or near-surface examination techniques for detection of flaws at/or near the component surface; or 2) volumetric examination techniques for detection of flaws within the volume of the component. Surface examination techniques include:

penetrant testing (PT),
eddy current testing (ET),
thermal imaging, and
optical imaging techniques such as laser shearography, and digital image correlation (DIC)

Volumetric Examination Techniques Include:
  ultrasonic examination (UT), includes conventional and phased array UT, and guided wave UT
  bond testing—a form of UT
  radiography (RT)
Other NDE Techniques Include:
  tap-testing—an audio technique to detect areas of lack of bond in composite materials
  acoustic emission—use of piezo-electric sensors to detect changes in component strain The prime factor for performing comprehensive wind turbine blade inspections is the ability to examine large surface areas with little or no contact with the component surface. All of the above NDE methods have been used to perform examinations on wind turbine blades, and each will provide examination information within the scope of the technique's capability. There are advantages and disadvantages in applying any of these techniques to examine a wind turbine. For example, ultrasonic examination is very good for detecting subsurface lack of bond, and other structural bonding anomalies. However, the ultrasonic transducer/probe must in contact with the part and only a small area/volume underneath the probe is examined. Acoustic emission (AE) is used during blade testing to detect the stress waves (audio) that are released in a material when it is subject to an external load/stress. Multiple AE sensors must be attached to the component and the component loaded in order to detect the presence of potential flaw locations. While AE is practical for monitoring blade testing activities, it would be difficult to implement for post-fabrication and in-service examinations of blades.

Radiography requires access to both sides of a component to place the source and film, which is not always practical. For thermal imaging, the detection capability is related to the thermal depth of penetration which may be limited due to the ability to heat-up of the large examination area.

Currently, visual examination is predominately used to determine the condition of wind turbine blades. No other NDE method has been developed that will provide a fast assessment of the overall structural integrity of the blade. With surface areas from 65 to 278 sq. meters (700 to 3,000 sq. ft.), or more, wind turbine blade inspection pose formidable challenges for both manufacturing and field inspection. In order to develop a better alternative to visual examination, an NDE technique should be able to examine these large surface areas, with little or no contact with the component surface.

Laser shearography NDE using current portable thermal, vacuum and acoustic energy stress techniques are well known, such as is disclosed in U.S. Patents, Newman et al, U.S. Pat. Nos. 5,146,289; 5,257,088; and 6,717,681, the entire disclosures of which are incorporated by reference as if set forth fully herein. However, such techniques require the shearography camera be in relatively close proximity, typically from 10 inches to 10 feet, to the area on the test part being inspected. This requirement is caused by environmental degradation of the image due to test part motion, air currents with temperature and density gradients that refract the laser light used to illuminate the test object surface or light that reflects from the surface to the camera. An additional limitation in current shearography systems is the image degradation due to relative movement between the camera and the test object. Many portable shearography systems require physical placement of the inspection devices on the blades requiring rope, crane or sky lift platforms to gain access to blade areas requiring inspection.

SUMMARY OF THE INVENTION

The present invention describes a long range shearography camera capable of imaging deformation derivatives at a distance of at least 250 ft. (76.2 meters) coupled with a blade stressing mechanism incorporating either thermal or internal blade pressurization for the purpose of detecting remotely and at high speed, changes in the structural integrity of the installed wind turbine blade on the tower.

The shearography camera is a common path imaging interferometer that processes images showing the first derivative of the out-of-plane deformation of the test part surface in response to a change in load. Sensitivity is generally in the vector direction from the object surface to the camera and, in practice, a shearography camera can image changes resulting from deformations as small as 2 to 20 nm. Shearography cameras have a built-in laser light source to illuminate an area on the test part. The field of view can range from several square centimeters to several square meters, depending on the maximum allowable discontinuity size. The laser light reflects from the surface of the test part and enters the shearography camera aperture (FIG. 1). A beam splitter and two mirrors are used to create two separate images of the test area, which are combined on a charge coupled device (CCD) detector.

A method of calibrating a shearography image according to a first aspect of the invention includes steps of projecting two beams of structured light on to an object to form two dots having a known distance of separation, imaging the two dots with a shearography system and calibrating the shearography system using the known distance of separation.

A method of performing a shearographic inspection of an object according to a second aspect of the invention includes steps of projecting two beams of structured light on to an object to form two dots having a known distance of separation, imaging the two dots with a shearography system, calibrating the shearography system using the known distance of separation; and using the shearography system to perform inspection of at least a portion of the object.

A method of inspecting a wind turbine blade according to a third aspect of the invention includes steps of stressing at least a portion of the wind turbine blade using a pressure differential; and scanning at least a portion of the wind turbine blade using laser interferometric imaging.

A method of retrofitting a wind turbine system for remote testing of the structural integrity of wind turbine blades according to a fourth aspect of the invention includes steps of creating a pressure seal in order to isolate an internal space of a wind turbine blade; and coupling pressurization equipment to the internal space of the wind turbine blade.

A method of inspecting a wind turbine blade according to a fifth aspect of the invention includes steps of stressing at least a portion of the wind turbine blade; and scanning at least a portion of the wind turbine blade using laser interferometric imaging.

A method of inspecting a wind turbine blade according to a sixth aspect of the invention includes steps of applying a thermal stress to at least a portion of the wind turbine blade, thermographically imaging the portion of the wind turbine blade; and analyzing the thermographically image.

A method of remotely inspecting a cantilevered object according to a seventh aspect of the invention includes steps of imaging a remote cantilevered object with a shearography camera, wherein a distance between the shearography camera and the remote cantilevered object is substantially within a range of about 50 feet to about 1500 feet; and analyzing the remote cantilevered object with a shearography system.

A method of remotely inspecting a wooden turbine blade according to an eighth aspect of the invention includes steps of applying a thermal stress to a wind turbine blade; imaging at least a portion of the wind turbine blade using a shearography camera, wherein a distance between the shearography camera and a wind turbine blade is substantially within a range of about 50 feet to about 1500 feet; and analyzing the wind turbine blade with a shearography system.

A method of remotely inspecting a wind turbine blade according to a ninth aspect of the invention includes steps of stressing at least a portion of the wind turbine blade using a pressure differential; and scanning at least a portion of the wind turbine blade using a shearography system having a camera, wherein a distance between the camera and the wind turbine blade is substantially within a range of about 50 feet to about 1500 feet.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
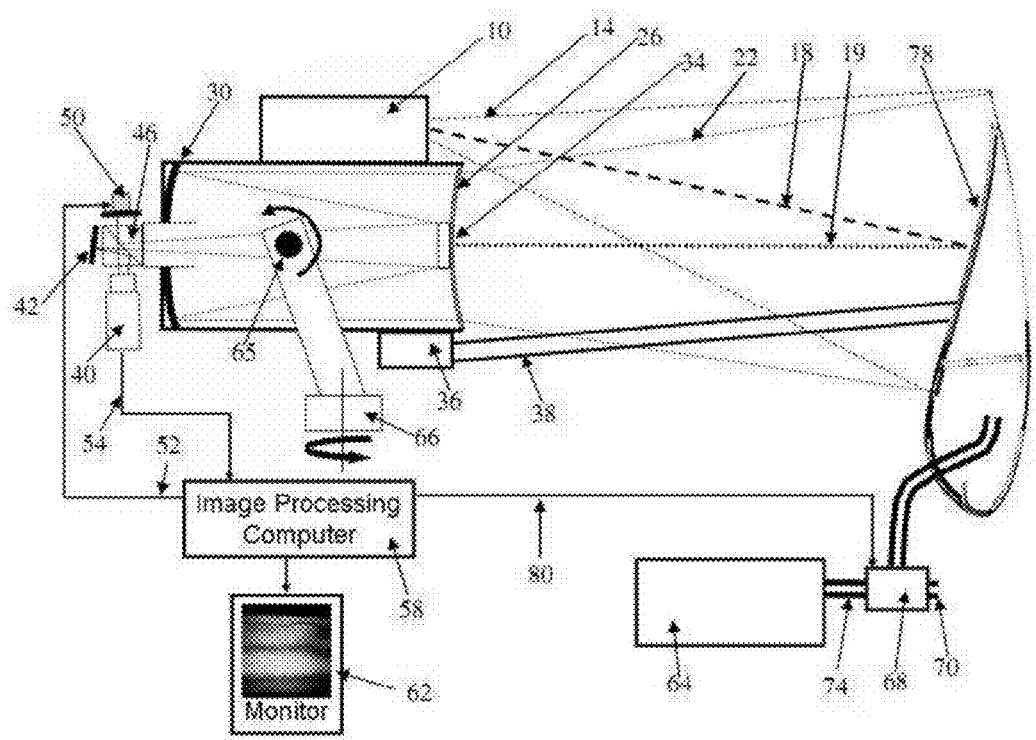
FIG. 1 is a schematic diagram of a telescopic shearography camera for remote nondestructive testing of an object according to a preferred embodiment of the invention.
Figure 2:
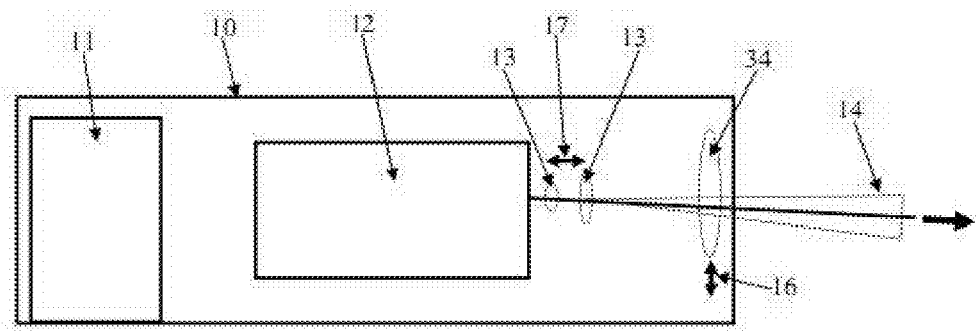
FIG. 2 is a diagram of a laser beam illuminator with expansion and beam steering optical elements. The beam steering optical element is used to aim the expanded laser beam to optimally illuminate the test area on the surface of the remote test object.

Referring now to the drawings, wherein like reference numerals designate corresponding structure throughout the views, and referring in particular to FIGS. 1, 2, 3, 4, 5, 6, 7, 8, a system for nondestructive evaluation according to a preferred embodiment of the invention may be used to perform remote nondestructive testing of structures.

Laser Shearography is normally performed with a test set up with the distance from the camera to the target anywhere from several inches to 4-8 feet. Shearography is well established as an industrial tool for nondestructive testing and specific reference is made to the ASTM Standard Practice Guide E2584-07, *Shearography of Polymer Matrix Composites, Sandwich Core Materials and Filament Wound Pressure Vessels for Aerospace Applications*, incorporated herein by reference as if set forth fully herein. U.S. Pat. Nos. 4,887,899 and 5,011,280 to Hung and U.S. Pat. No. 5,094,528 to Tyson et al., the entire disclosures of which are incorporated herein by reference as if set forth fully herein, disclose such shearography systems.

One advantageous aspect of the shearography system that is constructed according to the preferred embodiment of the invention is that it extends the distance range for performing shearographic nondestructive testing. The system has particular utility for performing nondestructive shearographic testing on large objects such as wind turbine blades for electricity generation, both during the manufacturing process and in-situ on a tower where the distances from the shearography camera to the target area on the blade to be examined exceeds the range of conventional shearography systems.

Challenges that have been encountered in attempts to perform shearography at distances include the degradation of image quality due to environmental effects such as wind-induced test part motion and vibration, variations in air density causing refraction of the laser light and the requirement for applying the necessary small change in stress uniformly over an area on large objects to allow the detection of defects, operational damage, and damage from environmental factors such as over-stress from excessive wind loads. In addition, the detection of structural changes due to lightning strikes and cyclic fatigue loading is critical to reliable operation of a shearographic inspection system. In the case of wind turbine blades, the rapid detection of disbonds and cracks at the trailing edge adhesive bond line is important, as that joint and the interface of the blade shell at the trailing edge carries much of the torque loads on the blade during operation. Other critical joints are the shell to spar bonds and the structural integrity of the leading edge.

Internal blade pressurization changes and thermal shearography techniques have been demonstrated by the inventor as being effective for the detection of these and other defects in wind turbine blades.

FIG. 1 is a diagram showing the basic configuration of a long distance shearography telescope. This diagram shows a Schmidt-Cassegrain type optical arrangement, which provides an efficient light gathering capability in a relatively compact size. However, other telescope types including but not limited to Ritchey-Chrétien, Newtonian and refractor type telescopes may be employed. The illumination laser assembly 10 includes a laser 12, operating at a wavelength at or near the frequency for peak quantum efficiency of the CCD video camera detector 40, producing a beam that is expanded through a lens assembly 13. The expansion angle is determined by lens separation 17 and the focal length of the lenses selected to produce an illuminated area on the test object 78, at a distance. Preferably, the distance is substantially within a range of about 50 feet to about 1500 feet, more preferably substantially within a range of about 100 feet to about 1000 feet, and most preferably substantially within a range of about 200 feet to about 700 feet. The expanded laser beam is further expanded by the beam steering lens 34 to produce the final expansion angle of illumination beam 14.

The laser beam steering lens may also be adjusted in a plane perpendicular to the axis of the beam 18 in any direction to adjust the angle laser beam 14 to approximately intersect the main axis of the shearography camera 19 at the surface of test object 78. In addition, the illumination beam 14 may be adjusted off the main axis of the shearography camera by the operator if for any reason a more uniform illumination of the test area is obtained. This may be due to surface color, reflectivity or surface contour. Laser light 22, reflecting from the diffuse surface of the test object 78, enters the telescope passing through the corrector plate 26, reflecting from and being focused by the main telescope mirror 30 to the secondary mirror 34. Laser light 22, from the test object 78 then enters the shearography optics consisting of a beam splitter 46 and two mirrors 42 and 50. Mirror 42 is adjusted off axis to create a second displaced image of the test object. The laser light continues into the CCD camera 40, and the images are digitally streamed through line 54 to the image processing computer 54.

The sheared laser illuminated image pairs interfere with each other and are referred to as an interferogram.

The phase of light from each point on the part in one image is interfered with the phase of light from its paired point in the corresponding image. This pixel pairing is determined by the shear vector, which has an angular component and a magnitude of distance component. The light intensity detected by each pixel in the CCD camera 40, is determined by the complex summation of the light from these two points on the target.

When a portion of the test object 78 such as a wind turbine blade is stressed, the test part will not deform uniformly if nonhomogeneities such as impact damage, voids, disbonds, cracks sheared core and variations in bond-line width are present. If light from adjacent points on the test object 78, separated by the shear vector, is located on a disbond, it will be phase shifted with respect to light from well-bonded material, due to a change in the distance traveled from the test part to the shearography camera.

The phase stepper applies a π/2 phase step to mirror 50 at a video frame rate of about (30 frames/s) or higher. Shearography NDT involves quantitative determination of the deformation derivatives between two stain states. As the applied load on the test object is changed, two sets of phase-stepped images are captured, and the phase calculation is performed in the image processing computer 58, for each pixel over the image, using the following equation for the four-phase step method:

$$\Delta(x, y) = \tan^+\left(I_8[x,y] - \frac{I_6[x,y]}{I_5[x,y]} - I_7[x,y]\right) - \tan^+\left(I_4[x,y] - \frac{I_2[x,y]}{I_1[x,y]} - I_3[x,y]\right)$$

where
$I_1$ through $I_8$ are eight sequentially phase-stepped captured images, described by the following:

$$I_1(x,y) = \tan^- I'(x,y) + I''(x,y)\cos(\Phi[x,y])$$
$$I_2(x,y) = I'(x,y) + I''(x,y)\cos\left(\Phi[x,y] + \frac{\pi}{2}\right)$$
$$I_3(x,y) = I'(x,y) + I''(x,y)\cos(\Phi[x,y] + \pi)$$
$$I_4(x,y) = I'(x,y) + I''(x,y)\cos\left(\Phi[x,y] + \frac{3\pi}{2}\right)$$

After these four image frames are captured, a small stress is applied to the test object followed by the subsequent capture of four additional phase stepped video frames:

$$I_5(x,y) = I'(x,y) + I''(x,y)\cos(\Phi[x,y] + \Delta[x,y])$$
$$I_6(x,y) = I'(x,y) + I''(x,y)\cos\left(\Phi[x,y] + \Delta[x,y] + \frac{\pi}{2}\right)$$
$$I_7(x,y) = I'(x,y) + I''(x,y)\cos(\Phi[x,y] + \Delta[x,y] + \pi)$$
$$I_8(x,y) = I'(x,y) + I''(x,y)\cos\left(\Phi[x,y] + \Delta[x,y] + \frac{3\pi}{2}\right)$$

and where
I'=the bias intensity
I''=the modulation intensity
Φ=the random phase variable due to reflection of the laser light from a diffuse surface
Δ=a quantity directly proportional to the differential displacement due to the test part deformation from the applied load change.

The long distance production or in-situ shearography inspection may also use alternate imaging interferometers, such as the birefringent type shearing optical arrangement, is disclosed by the previously referenced patents to Y. Y. Hung and Newman et al. The result yields a phase map showing the deformation derivative for a deformed surface of test object 78. The phase map image may then be unwrapped and displayed on monitor 62. To detect defects in test objects such as wind turbine blades a small stress must be applied. Thermal stress and mechanical stress such as that created by blade pressurization are two methods according to preferred embodiments of the invention for shearography inspection of wind turbine blades and will be discussed in detail herein.

Alternate image processing techniques for the interferogram images may be used wherein single images are captured while the pressure load on the blades is changing and mirror 50 in the shearography camera is moved by piezoelectric phase shift device continuously by small increments such as π/2. The changes in speckle intensity correlate with surface motion on the blade, allowing the outline of critical blade bond lines to be measured. These images may be further averaged or processed.

The shearography image of a test object 78 contains three types of data. First, is the graphic pictorial data represented as a two dimension image in grey level or color mapping changes in numerical deformation derivative as a result of changes in an applied load. Second, the image is calibrated in terms of the image scale, as measured in pixels per inch (or cm) in the plane of the surface of the test object 78. For contoured test objects, the image scale may vary over the field of view by dividing the field of view into a grid and measuring the image scale in each grid to what ever resolution is required. Conversely the image scale may also be measured at the site of an anomaly during the measurement of the defect.

The third type of data contained in a shearogram is the shear vector. As defined in ASTM E2584-07, the shear vector is the measured offset of the two images of the test area on the test object 78, created with the shearography optical system. The angle and the amount of shear is measured on the surface of the test part. Conventional practice for determining the shear vector is to manually place a physical calibration card in the plane of the surface of the test object 78 with two dots separated by the desired shear vector offset distance and oriented at an angle equal to the desired shear vector angle. Adjusting the angle of mirror 42 in the x or y direction, or both, causes the left dot to overlay the other creating two images of test object 78, as seen through the shearography optics, with the desired shear offset amount and angle. The shear vector is usually measured once in the middle of the field of view. However, as with the image scale, the shear vector for contoured parts may be measured multiple times over the field of view or just at the site for measured anomalies. As the test object 78 distance or height increases, the use of a calibration card for calibrating the shearography image becomes impractical and slow. In addition, for automated scan testing of the test object 78, the distance and angle to the target may change requiring repeated calibration of the shearography camera.

Figure 3:
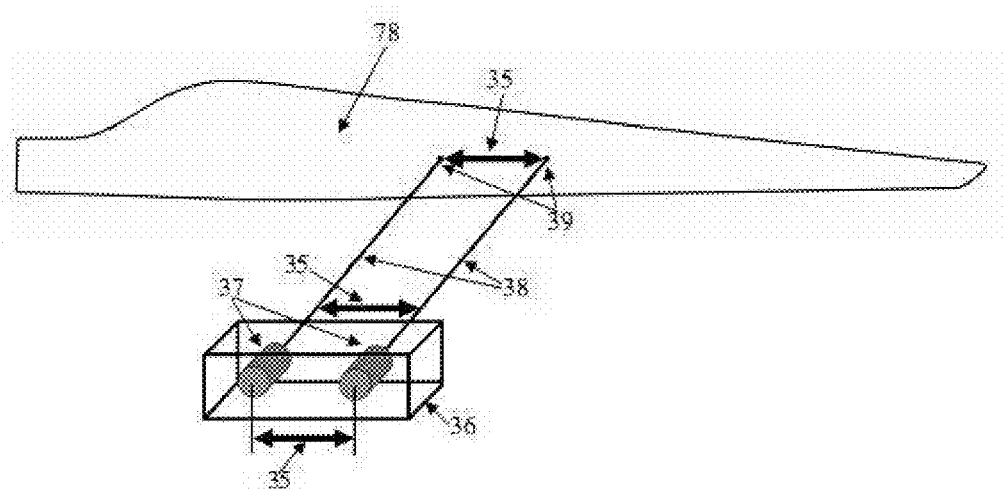
FIG. 3 is a diagram showing the laser spot project for projecting parallel laser beams from the shearography camera to the test object to provide image scale in pixels/inch and for determining the shear vector of the shearography camera.

The use of the laser spot projector, as shown in FIG. 3, allows highly accurate calibration of the shearography image even for distant test objects. Two beams of structured light, preferably laser light sources 37, are mounted in a frame or block 36, and adjusted to provide substantially parallel beams 38 with a known separation distance of 35. The laser beams 38 create two laser dots, 39, on the surface of test object 78, that have the same, known distance of separation at any distance to the target.

Preferably, the two beams of structured light are projected onto the test object 78 at a distance that is substantially within a range of about 50 feet to about 1500 feet, more preferably substantially within a range of about 100 feet to about 1000 feet, and most preferably substantially within a range of about 200 feet to about 700 feet. In the preferred embodiment, the test object 78 is at least a portion of a wind turbine blade, although the method could alternatively be used to inspect any one of a wide array of remote objects. Preferably, the test object 78 is contoured, although in alternative embodiments flat, unfeatured objects could be assessed.

The two laser dots 39 are imaged with a shearography system having a shearography camera. The shearography system is then calibrated using the known distance of separation. Through the shearography camera, the image scale in pixels/inch (cm) can be determined using software on a computer. This involves dividing the known distance between the two laser dots 39 by the number of pixels in order to determine the image scale. The shear vector angle can be measured manually or automatically using a computer. This involves measuring or calculating the angle of separation and the magnitude of distance between common points on the two displaced images. Similarly, the direction of shear can also be determined, either manually or automatically using a computer. Automatic measurement and setting of the shear vector is important for rapid automatic scanning of test objects 78 with contours, varying distances to the target. In addition, a computer controlled laser spot projection can be used to rapidly and automatically measure the image scale and shear vector over the entire field of view.

FIG. 1 shows further the inclusion of equipment to allow the internal pressurization of hollow test objects, such as wind turbine blades, in order to stress the test object for purposes of nondestructive testing, preferably using laser interferometric imaging such a shearography or thermography. Internal pressurization is performed by inducing a pressure differential between the internal space within the wind turbine blade and external ambient pressure conditions. In the preferred embodiment, the internal pressurization is positive, meaning that there is a positive pressurization within the internal space relative to external ambient pressure conditions.

Preferably, the positive pressurization relative to external ambient conditions is substantially within a range of about 0.01 psi to about 10 psi, more preferably substantially within a range of about 0.02 psi to about 7 psi and most preferably substantially within a range of about 0.05 psi to about 3.5 psi.

Wind turbine blades are typically constructed with adhesively bonded shells around a spar that supports the lift loads that creates the torque forces necessary to rotate the shaft of an electrical generator. The use of mechanical stressing, preferably embodied as internal blade pressurization, causes the aerodynamic shell to slightly inflate in unsupported areas and to be constrained at adhesive bond lines, such as the trailing edge or at the spar or spar cap joints, where forces are symmetrically balanced by the loads on the high pressure and low pressure sides of the wind turbine blade. Cracks at these joints or areas with less adhesive than required may be imaged due to the additional width of the crack, allowing the aerodynamic shell to expand more than that shown during a baseline scan of the test blade made during the manufacturing process or when first installed in the field.

Figure 9:
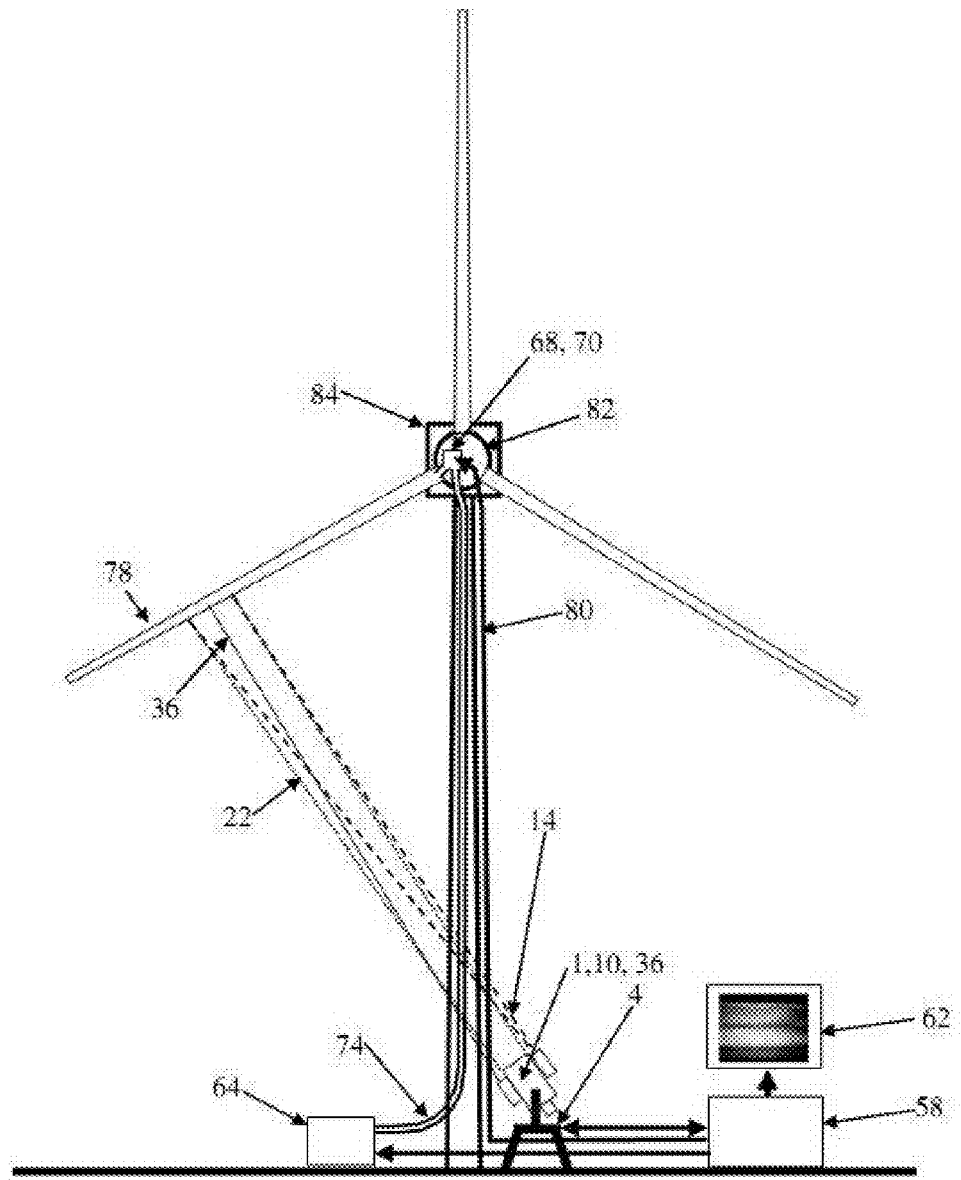
FIG. 9 is a schematic drawing showing an assembly for in-situ shearography inspection of wind turbine blades.

The air blower 64, provides a flow of air to tube 74, which is a built-in conduit or a flexible hose to conduct air under pressure to a three way control valve 68. Signal line 80, provides electric signals to open or close the valve to alternately admit air to the internal cavities of the test object 78 or to allow the pressurized air within the test object 78 to exhaust to the atmosphere through vent line 70. As shown in FIG. 9, the particular time versus pressure profile may be programmed into the computer and may include increasing the pressure inside the test object to a set bias pressure, to cause crack opening, followed by cyclic modulation of the pressure during shearography data acquisition.

Figure 4:
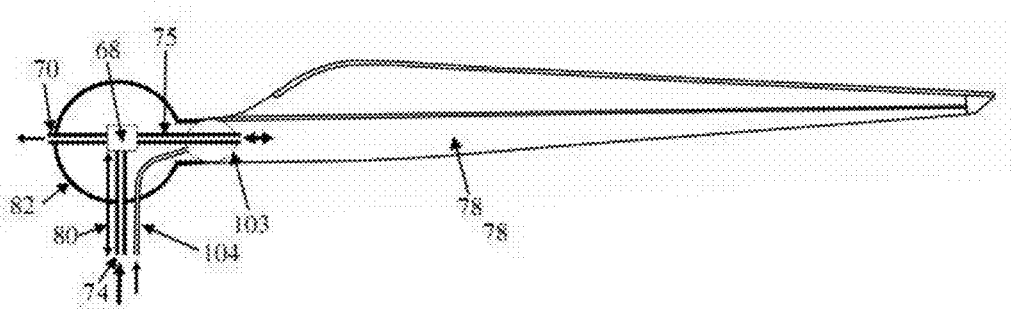
FIG. 4 is a schematic diagram of an inflatable blade seal to allow pressurization of a wind turbine blade in manufacturing or in-situ on the tower for shearography inspection.
Figure 6:
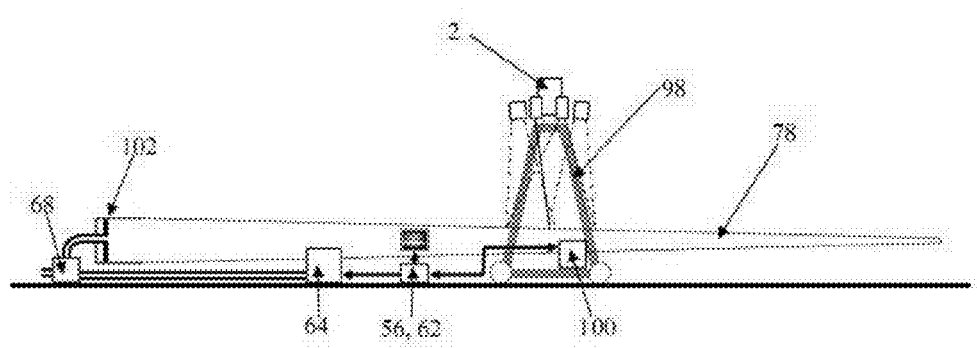
FIG. 6 is a schematic diagram showing equipment configuration for shearography inspection of wind turbine generator blades during manufacturing.
Figure 7:
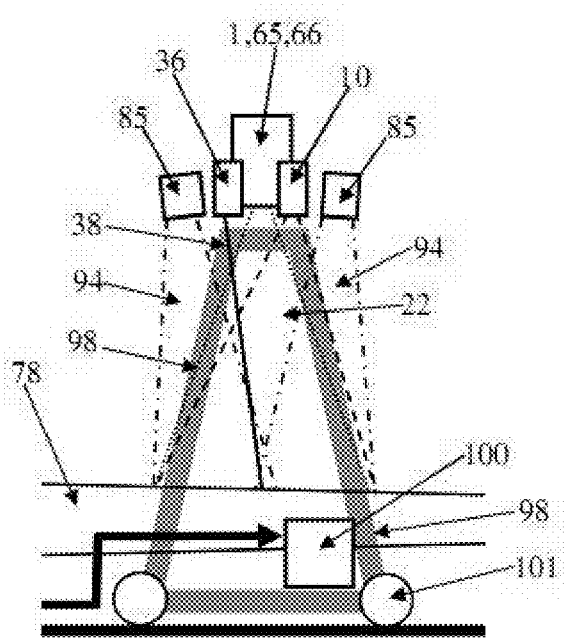
FIG. 7 is a close up schematic diagram of a shearography camera on a scan gantry with equipment for thermal and wind turbine blade pressurization shearography.
Figure 8:
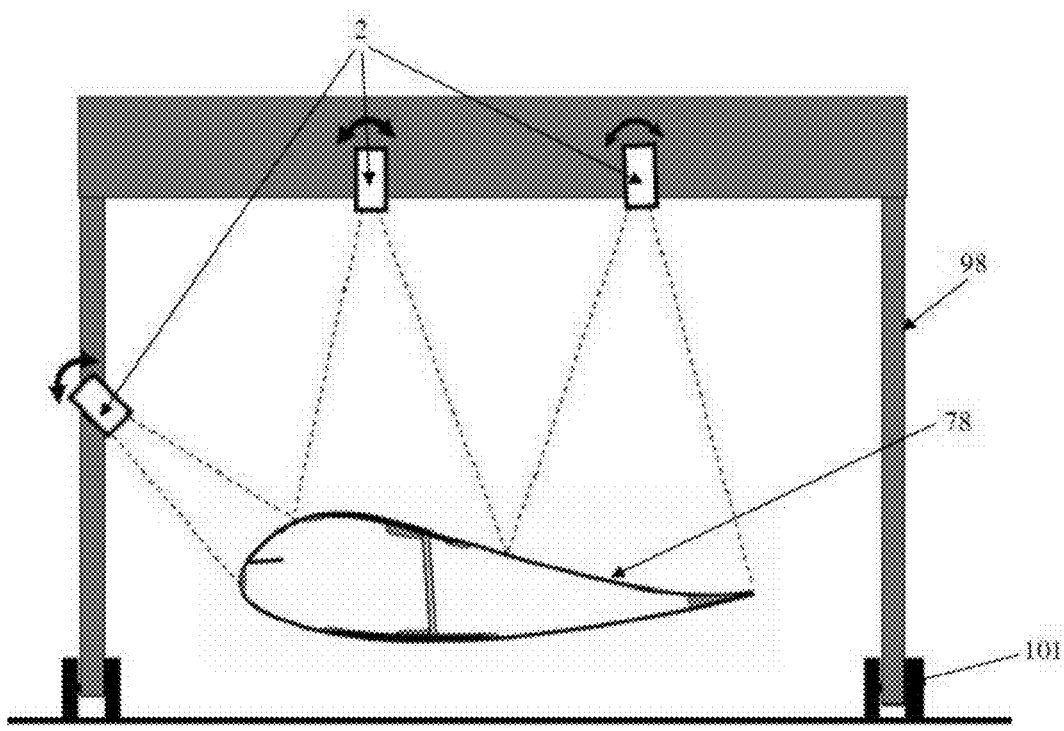
FIG. 8 is a schematic depiction showing multiple shearography camera systems on a scan gantry.

Internal Pressurization shearography of wind turbine blades can be performed during the blade manufacturing process as shown in FIGS. 6, 7 and 8 or in-situ installed on the tower, from the ground as shown in FIG. 9. In both cases a blade sealing mechanism is used to enclose the internal cavity of the blade, generally at the man-way access port. The wind turbine blade can be sealed using a variety of means, one, as shown in FIG. 4, being the use of a rubber fabric reinforced, inflatable seal, 103, with a tube 75, passing through it to provide air flow into and out of the blade cavity from the 3 Way Control Valve 68. Tube 104 provides inflation air for this inflatable seal, which is sized to provide a tight fit against the inside cylindrical shaped root end of the blade and resist the internal pressure build up in the blade interior during shearography inspection.

In addition, manufacturers can build in pressurization piping to pressurize the blades from a single, or multiple convenient points including a pressurization manifold located at the base of each wind turbine tower. Such an arrangement would allow rapid in-situ inspection of blades without needing access to the tower hub. Alternatively, a small air blower can be built into the generator housing and controlled from the ground or provided appropriate electrical signals such as a bidirectional data link to the shearography test system on the ground.

In cases where a method of inspecting a wind turbine blade is performed in situ, at least a portion of the wind turbine blade is preferably scanned using laser interferometric imaging, most preferably with a shearography system having a shearography camera, at a distance that is substantially within a range of about 50 feet to about 1500 feet, more preferably substantially within a range of about 100 feet to about 1000 feet, and most preferably substantially within a range of about 200 feet to about 700 feet. Scanning is preferably performed while the wind turbine blade is being either mechanically or thermally stressed, or both. The shearography system and a shearography camera may be mounted on the ground below the wind turbine blade, either as part of a mobile installation or a stationary ground mounted unit. Alternatively, the shearography system and shearography camera may be mounted to the tower of the wind turbine system. The latter embodiment is preferable for inspecting marine wind turbine installations.

Figure 10:
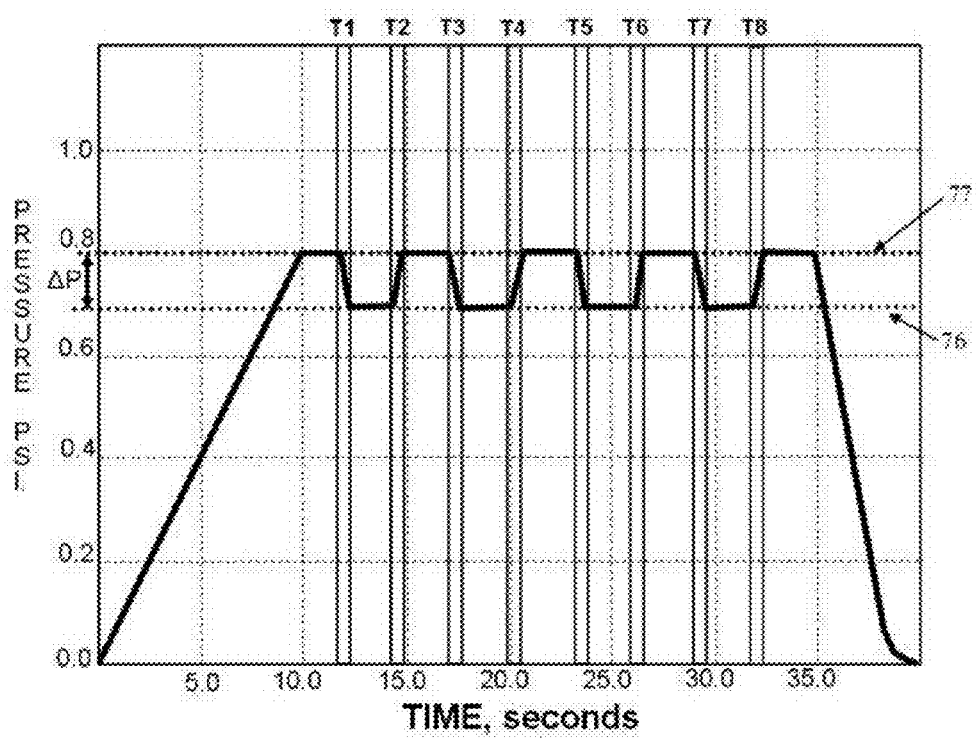
FIG. 10 is a diagram of a typical pressure versus time profile for wind turbine blade shearography pressurization. Eight shearography tests are performed at T1, T2 . . . T8 over a 20 second period.

FIG. 10 shows a typical Pressure versus Time profile for wind turbine blade shearography inspection using internal blade pressurization. In the preferred embodiment, the internal pressurization of the wind turbine blade is modulated during inspection with the shearography camera. Preferably, the modulation of pressure is a substantially regular pressure variation. Shearography data is acquired during the pressure change +ΔP, increasing from the bias pressure 76 to the test pressure 77 or −ΔP, decreasing from the test pressure 77 to bias pressure 76. Shearography phase data taken during decreasing pressure, −ΔP must be inverted to match the phase of data acquired during increasing pressurization +ΔP. As may be gleaned from Pressure versus time profile, shearography data is acquired rapidly. Here eight tests are accomplished at T1, T2 . . . T8 over a period of 20 seconds. Typical fields of view on the test object, such as a wind turbine blade, with the appropriate laser and support equipment describe herein may be 1 to 2 sq. meters/test, providing inspection at a rate here, of up to 48 sq. meters per minute, assuming ideal environmental conditions.

The internal pressurization within the wind turbine blade may be monitored over a period of time. The rate of decay of the internal pressurization is indicative of the presence and magnitude of cracks that may be present in the outer shell of the wind turbine blade. A baseline rate of pressure decay may be established for a particular wind turbine blade during the manufacturing process, upon the initial installation of the wind turbine blade in a wind power installation, or periodically over the lifetime of the wind turbine blade. A significant increase in the rate of pressure decay in comparison to the baseline rate may be used as an indication that cracks may have developed in the scan of the wind turbine blade, necessitating more thorough nondestructive testing.

An additional requirement is a computer controlled blade tracking system whereby the telescopic shearography camera is scanned in steps over both the high and low pressure sides of the blades in-situ. This may include secondary laser pointers positioned by the operators to place laser designator spots at strategic points on the blade. The software can then seek and lock onto each target designator spots to perform a shearography test at that location. Alternately, the operator can sight in the telescope on key targets at the blade tip and the root. Computer software then moves the shearography system in steps with each test cycle, over the surface of the blade. Such a system has a additional benefit of preventing uncontrolled skyward laser beam projection, which could potentially interfere with aircraft and/or satellites.

All other shearography blade test equipment can be built into an appropriated truck or van to transport the equipment quickly and efficiently to the test site for each wind turbine generator. Manual, electric or hydraulic systems to stabilize the vehicle during the tests to eliminate movement for the vehicle suspension system may be included. Alternatively, the shearography system can be lowered to the ground using a manual or automatic lift to achieve stability with respect to the blade targets.

During the time between tests the shearography camera, 1, would be re-aimed, using the computer controlled tilt motor drive 65, and the pan motor drive 66 for the next test area on the test object 78. Mounted on a scan gantry 98, such as shown in FIGS. 6 and 7, the gantry would move manually or automatically with the Gantry motor drive and Controller receiving signals from the image processing computer when and how much to move down the length of the blade 78. The test object is preferably a remote cantilevered object such as a wind turbine blade that is substantially constrained to move in one direction. Preferably, a direction of the wavefront received by the shearography camera 1 is substantially parallel to the direction in which the wind turbine blade is substantially constrained to move.

In addition, the shearography camera 1, with its pan and tilt motor drives and encoders, as well as the thermal stress units 85, altogether referred to as 2, can be moved by the gantry to multiple inspection points and scan a programmed pattern. In this way the entire test object is inspected, accounting for changes in shape and geometry such as blade taper over its length. These images may to stitched together to form a single image of the entire test object 78 or blade. The shearography calibration data can be merged to allow measuring defect indication or features across images anywhere on the test object.

Multiple shearography cameras 1, with laser spot projectors 36, laser units 10 and thermal stress units 85, as well as the motorized pan and tilt motion systems 85, 86, may be mounted on a gantry as shown in FIG. 8, to perform a single pass inspection of each side of the blade, flipping the blade to inspect the other side.

Figure 5:
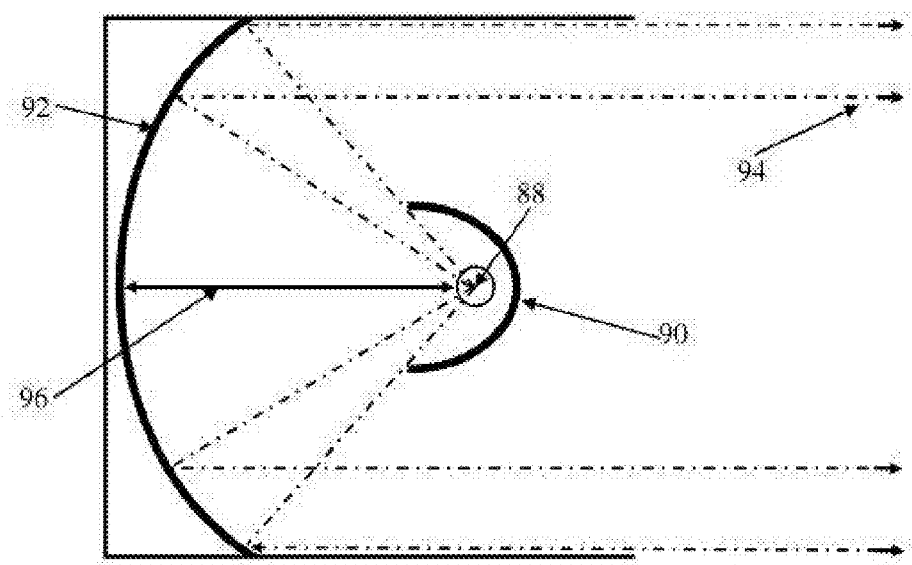
FIG. 5 is a schematic diagram of long distance thermal source for in-situ inspection of wind turbine electricity generator blades.

FIG. 5 shows a Thermal source for surface heating of test objects at a distance during shearography inspection. Variations in the local coefficient of thermal expansion caused by structural anomalies is easily detected with shearography. Cracks at the trailing edge adhesive bond, impact damage, delaminations of the shell are easily detected. In practice, energy densities substantially within a range of about 2-50 watts/sq. inch are used with heating times that are substantially within a range of about 1-20 seconds, depending on material emissivity and thickness. Thermal sources typically range substantially from about 2 to 20 kW depending on the application, target range and the field of view. The heat source 88 is preferably a small filament quartz lamp in the 1-2 kW power range, although arc lamps or other sources of IR may be used. A small reflect, 90 mounted close to the source 88 may be used to focus the radiant energy on the primary mirror 92, which in turn focuses the beam in the direction of the test object 78. Adjusting the distance between the source 88 and the primary reflector 92 will change the expansion angle of the radiant energy and hence the energy density on the surface of the test object or wind turbine blade. This thermal heating device may be attached to the shearography camera to provide thermal stressing of the test object at the location on the test object where the shearography camera is aimed. This thermal source may be manually or remotely aimed so the center of the radiant heat on the center of the shearography camera field of view.

Thermographic imaging can alternatively be used to inspect the wind turbine blade after it has been thermally stressed using the thermal source. The thermographic imaging can be used on its own or in conjunction with laser interferometric imaging such as shearographic imaging. For example, a thermographic imaging system such as that disclosed in U.S. Pat. No. 7,083,327 to Shepard, the entire disclosure of which is hereby incorporated by reference as a set forth fully herein, could be used. Such a system is capable of detecting subsurface defects and discontinuities by changing the dimensions of the defect while or immediately after the part is heated. The specimen's surface temperature is monitored over time to detect the defect. Such a system typically includes an image generator, such as an infrared camera, and structure for changing the pressure on a surface of the specimen being tested to stress and unstress the specimen. The pressure changes cause subject portions of the object being tested to move relative to each other, separating and/or shifting the walls of the defect to create thermal discontinuities in the specimen and increase the thermal contrast between the defect and the surrounding material.

In one embodiment of the invention, thermographic imaging and shearographic imaging are integrated into a single system. The thermographic imaging is preferably performed at distance using a telescope, which could be embodied as either a Cassegrain reflector or a Newtonian telescope. The thermography camera should be sensitive in the long IR wavelength band, typically from 8 to 16 nm. wavelength, with all of the optical elements in the telescope capable to high optical efficiency at these wavelengths. Reflecting telescopes, especially with gold coated mirrors or other coatings optimized for maximum reflectivity the long IR band.

In the preferred embodiment, the thermal source is at a distance from the test object, which is preferably a wind turbine blade, that is substantially within a range of about 50 feet to about 1500 feet, more preferably substantially within a range of about 100 feet to that 1000 feet and most preferably substantially within a range of about 200 feet to about 700 feet. The thermal source preferably directs focused radiation to the test object, which is preferably either infrared radiation or microwave radiation. The test object may be provided with a special coating or layer that is constructed and arranged to heat the outer shell of the test object when subjected to microwave radiation.

In another alternative embodiment of the invention, an acoustic input such as a vibration may be applied to at least a portion of the wind turbine blade in order to induce the opening of cracks. As another alternative, the natural vortexes created by wind passing over the wind turbine blade may induce crack opening without added vibration.

FIG. 9 shows the test set up for shearography inspection of wind turbine blades in-situ on the tower. This test requires the blades be feathered and stopped into position allowing imaging of the high pressure downward facing side of one blade then moving the camera to image the downward facing low pressure side of another blade. The hub lock is released and the blades rotated 120 degrees and locked again and the inspection cycle is repeated twice until all surfaces of the blades have been inspected.

For this inspection, either thermal stress using the thermal source and/or internal blade pressurization is used to stress the blades during shearography inspection. For pressurization, air is provided by blower 64 through pipe or hose 74 to the three way valve, which is best placed in the generator nacelle 84, but could be placed on the ground with the blower. Either way, air flows into the blade to achieve the desire bias pressure and the internal blade pressure is then modulated at a frequency and pressure range determined by the volume of the blade and thickness of the materials. The bias pressure allows the blade to be kept at a relatively high pressure to increase flow rates and pressure changes without having to use a larger diameter control valve 68. Air is vented through the vent line 70 during the pressure drop portion of the modulation.

A method of retrofitting a wind turbine system according to one embodiment of the invention is preferably performed by creating a pressure seal in order to isolate an internal space of a wind turbine blade, and coupling pressurization equipment such as the blower 64 described above to the internal space of the wind turbine blade. The pressurization equipment is preferably constructed and arranged to pressurize the internal space of the wind turbine blade sufficient to cause the opening of any cracks that may exist in the outer shell of the wind turbine blade. Preferably, the pressurization equipment is constructed and arranged to pressurize the internal space of the wind turbine blade with respect to ambient pressure conditions at a pressure that is substantially within a range of about 0.01 psi to about 10 psi, more preferably substantially within a range of about 0.02 psi to that 7 psi and most preferably substantially within a range of about 0.05 psi to about 3.5 psi. Alternatively, the step of providing pressurization equipment could be performed by installing a manifold that is accessible at ground level.

Shearography inspection requires relative stability between the shearography camera and the test object. When the relative motion of the test object exceeds the distance required to phase shift a laser light reflected from the surface of the target during the CCD, 40, exposure time the interferometric data is generally lost. Further, a test object such as a wind turbine blade can be considered as a double pendulum exhibiting seemingly chaotic motion. Without a repetitive harmonic motion, synchronizing shearography data capture with the test object motion is not possible. Instead, other techniques such as streaming the computed shearography data and culling images with acceptable image quality provides a means for capturing data in a motion environment.

Figure 11:
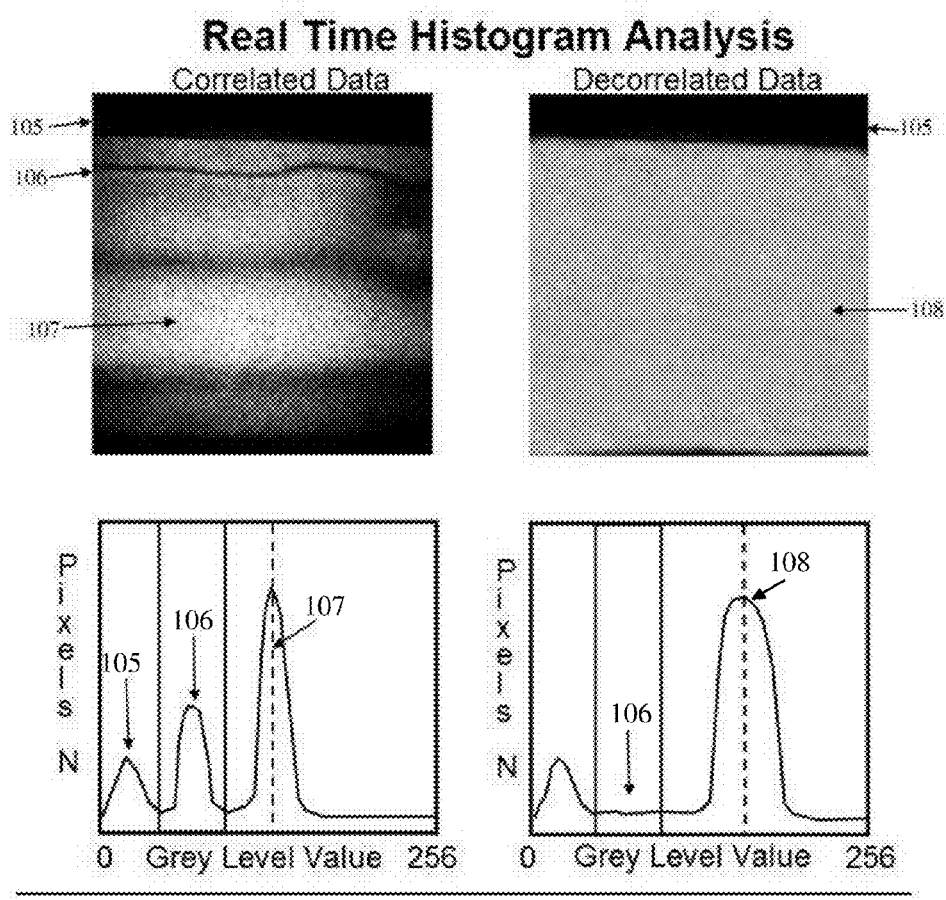
FIG. 11 is a real-Time histogram for the streaming real-time shearograms that can be analyzed using gates to detect the presence or absence of shearography signals and data with expected histogram values. Shearography data acquired during moments of excessive motion between the shearography camera and the test object results in a decorrelated image with no information for evaluating the blade.

One such technique is real-time histogram analysis, as shown in FIG. 11, which is a real-time histogram for the streaming real-time shearograms can be analyzed using gates to detect the presence or absence of shearography signals and data with expected histogram values. Shearography data acquired during moments of excessive motion between the shearography camera and the test object results in a decorrelated image with no information for evaluating the blade. Here, images are analyzed by counting the number of pixels for each grey level, from 0 to 256 for 8 bit data. As shown in FIG. 10, specific image features have pixels with grey level values in ranges. Dark area of images off the edges of the test part have a black level from 0 to 60. Dark indications of transition areas at adhesive bond lines with grey levels from 60 to 100. Bright areas of well bonded material have a grey from 100 to 200. Analysis software with gates and thresholds can be used to automatically select candidate images. For example, the pixel threshold count for values in the grey level range from 60 to 100, exceeds a set level. These shearography signals are typical of shearography signals from the inner edges of the trailing edge adhesive bond lines in the image shown. Shearography images taken with excessive test object motion, decorrelate and appear as shown in FIG. 11. These images would be discarded by the software.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of calibrating a shearography image, comprising:
   projecting two beams of structured light onto an object to form two dots having a known distance of separation;
   imaging the two dots with a shearography system; and
   calibrating the shearography system using the known distance of separation;

wherein the step of calibrating the shearography system using the known distance of separation comprises determining a shearography image scale in pixels per unit length.

2. A method of calibrating a shearography image according to claim 1, wherein the two beams of structured light are substantially parallel.

3. A method of calibrating a shearography image according to claim 1, further comprising determining a shear vector angle.

4. A method of calibrating a shearography image according to claim 3, wherein the step of determining a shear vector angle is performed by a computer.

5. A method of calibrating a shearography image according to claim 1, further comprising determining a direction of shear.

6. A method of calibrating a shearography image according to claim 5, wherein the step of determining a direction of shear is performed by a computer.

7. A method of calibrating a shearography image according to claim 1, wherein the step of projecting the two beams of structured light onto an object is performed at a distance that is substantially within a range of about 50 feet to about 1500 feet.

8. A method of calibrating a shearography image according to claim 7, wherein the step of projecting the two beams of structured light onto an object is performed at a distance that is substantially within a range of about 100 feet to about 1000 feet.

9. A method of calibrating a shearography image according to claim 8, wherein the step of projecting the two beams of structured light on to an object is performed at a distance that is substantially within a range about 200 feet to about 700 feet.

10. A method of calibrating a shearography image according to claim 1, wherein the object is a wind turbine blade.

11. A method of calibrating a shearography image according to claim 1, wherein the object is contoured.

12. A method of calibrating a shearography image according to claim 1, wherein the step of projecting the two beams of structured light onto an object is controlled by a computer.

13. A method of calibrating a shearography image according to claim 1, wherein the step of determining a shearography image scale is performed a computer.

14. A method of performing a shearographic inspection of an object, comprising steps of:
projecting two beams of structured light onto an object to form two dots having a known distance of separation;
imaging the two dots with a shearography system;
calibrating the shearography system using the known distance of separation; and
using the shearography system to perform inspection of at least a portion of the object;
wherein the step of calibrating the shearography system using the known distance of separation comprises determining a shearography image scale in pixels per unit length.

15. A method of performing a shearographic inspection of an object according to claim 14, wherein the two beams of structured light are substantially parallel.

16. A method of performing a shearographic inspection of an object according to claim 15, wherein the step of determining a shearography image scale is performed a computer.

17. A method of performing a shearographic inspection of an object according to claim 14, further comprising determining a shear vector angle.

18. A method of performing a shearographic inspection of an object according to claim 17, wherein the step of determining a shear vector angle is performed by a computer.

19. A method of performing a shearographic inspection of an object according to claim 14, further comprising determining a direction of shear.

20. A method of performing a shearographic inspection of an object according to claim 19, wherein the step of determining a direction of shear is performed by a computer.

21. A method of performing a shearographic inspection of an object according to claim 14, wherein the step of projecting the two beams of structured light onto an object is performed at a distance of the substantially within a range of about 100 feet to about 1000 feet.

22. A method of performing a shearographic inspection of an object according to claim 14, wherein the object comprises a wind turbine blade.

23. A method of performing a shearographic inspection of an object according to claim 14, wherein the step of projecting the two beams of structured light onto an object is controlled by a computer.

24. A method of performing a shearographic inspection of an object according to claim 14, wherein at least a portion of the object is contoured.

\* \* \* \* \*